US012605072B2

(12) United States Patent
Kim et al.

(10) Patent No.: US 12,605,072 B2
(45) Date of Patent: Apr. 21, 2026

(54) PHOTOACOUSTIC AND ULTRASONIC IMAGING DEVICE, AND IMAGING FORMING METHOD

(71) Applicant: OPTICHO INC., LTD., Pohang-si (KR)

(72) Inventors: Chul Hong Kim, Pohang-si (KR); Won Seok Choi, Pohang-si (KR); Eun Yeong Park, Incheon (KR); Seung Wan Jeon, Hwaseong-si (KR); Chang Yeop Lee, Pohang-si (KR); Moon Gyu Han, Pohang-si (KR)

(73) Assignee: OPTICHO INC., LTD., Pohang-si (KR)

( * ) Notice: Subject to any disclaimer, the term of this patent is extended or adjusted under 35 U.S.C. 154(b) by 0 days.

(21) Appl. No.: 18/268,271

(22) PCT Filed: Sep. 2, 2021

(86) PCT No.: PCT/KR2021/011871
    § 371 (c)(1),
    (2) Date: Jun. 19, 2023

(87) PCT Pub. No.: WO2023/017891
    PCT Pub. Date: Feb. 16, 2023

(65) Prior Publication Data
    US 2024/0293031 A1     Sep. 5, 2024

(30) Foreign Application Priority Data
    Aug. 10, 2021    (KR) ........................ 10-2021-0105598

(51) Int. Cl.
    A61B 5/00        (2006.01)
    A61B 8/00        (2006.01)
    A61B 8/08        (2006.01)

(52) U.S. Cl.
    CPC .......... A61B 5/0095 (2013.01); A61B 5/0035 (2013.01); A61B 8/0858 (2013.01);
    (Continued)

(58) Field of Classification Search
    CPC ... A61B 5/0095; A61B 5/0035; A61B 8/0858; A61B 8/0875; A61B 8/0891;
    (Continued)

(56) References Cited

U.S. PATENT DOCUMENTS

2005/0203399 A1 *   9/2005   Vaezy ...................... A61B 8/08
                                                      600/439
2013/0301380 A1 *  11/2013   Oraevsky ............. A61B 5/0095
                                                      367/7
(Continued)

FOREIGN PATENT DOCUMENTS

DE       102019213238 A1 *   3/2021
JP           H08611     *   1/1996
    (Continued)

OTHER PUBLICATIONS

Machine translation of Yeh et al (TW I431270) High-frequency Ultrasonic Imaging System and Method (Year: 2014).*
    (Continued)

*Primary Examiner* — Alexei Bykhovski

(74) *Attorney, Agent, or Firm* — LEX IP MEISTER, PLLC

(57)                    ABSTRACT

A photoacoustic and ultrasonic imaging device includes a laser light source configured to generate a laser, an ultrasonic wave source configured to generate an ultrasonic wave generation signal, an imaging probe including a laser emitter configured to receive the laser and emit the laser to a target and an ultrasonic transducer configured to receive the ultrasonic wave generation signal, emit an ultrasonic wave to the target, and detect a photoacoustic signal and an ultrasonic
                    (Continued)

START

FORM CONTOUR PROFILE OF TARGET — S100

PROVIDE LASER LIGHT AND ULTRASONIC WAVE TO TARGET ACCORDING TO CONTOUR PROFILE — S200

FORM PHOTOACOUSTIC IMAGE AND ULTRASONIC IMAGE OF TARGET BY DETECTING PHOTOACOUSTIC SIGNAL GENERATED FROM LASER LIGHT AND ULTRASONIC SIGNAL GENERATED FROM ULTRASONIC WAVE — S300

END signal generated and reflected from the target, and an operation unit configured to form an image of tissue in the target from the laser and an image of the tissue in the target from the ultrasonic wave on the basis of the photoacoustic signal and the ultrasonic signal detected by the ultrasonic transducer.

19 Claims, 8 Drawing Sheets

(52) U.S. Cl.
CPC .......... *A61B 8/0875* (2013.01); *A61B 8/0891* (2013.01); *A61B 8/4416* (2013.01)

(58) Field of Classification Search
CPC ....... A61B 8/4416; A61B 8/08; A61B 8/0833; A61B 8/00; A61B 5/00; A61B 8/4477; A61B 8/5261
See application file for complete search history.

(56) References Cited

U.S. PATENT DOCUMENTS

| | | | |
|---|---|---|---|
| 2021/0196386 A1* | 7/2021 | Shelton, IV | ..... A61B 1/000094 |
| 2023/0181148 A1* | 6/2023 | Mert | .................... A61B 8/0841 600/407 |

FOREIGN PATENT DOCUMENTS

| | | | | |
|---|---|---|---|---|
| JP | 2010-12295 | | 1/2010 | |
| JP | 2012-187394 | | 10/2012 | |
| JP | 2013-518673 | | 5/2013 | |
| JP | 2018-143778 | | 9/2018 | |
| JP | 2019-025217 | | 2/2019 | |
| JP | 2019-051016 | | 4/2019 | |
| JP | 2019-088346 | | 6/2019 | |
| JP | 2019-111435 | | 7/2019 | |
| JP | 2019-118457 | | 7/2019 | |
| JP | 2019-165836 | | 10/2019 | |
| JP | 2020-036898 | | 3/2020 | |
| KR | 10-2009-0088909 | | 8/2009 | |
| KR | 10-2014-0121451 | | 10/2014 | |
| KR | 10-2015-0120783 | | 10/2015 | |
| KR | 10-2018-0049977 | | 5/2018 | |
| TW | I431270 | * | 3/2014 | |
| WO | WO 2018172443 | * | 9/2018 | |

OTHER PUBLICATIONS

DE-102019213238—machine translation (Year: 2021).*
JP H08611 machine translation (Year: 1996).*
Hara et al (A New Sonographic Technique for Assessing Carotid Artery Disease: Extended-Field-of-View Imaging, the American Journal of Neuroradiology, vol. 20, Feb. 1999) (Year: 1999).*
Han, Moongyu, et al. "In vivo dual-modal photoacoustic and ultrasound imaging of sentinel lymph nodes using a solid-state dye laser system." Sensors 20 (Jul. 2, 2020): 3714. pp. 1-12.
KIPO, Office Action of KR 10-2021-0105598 dated Jun. 8, 2023.
JPO, Notice of Allowance of the corresponding Japanese Patent Application No. 2023-543082, issued on Nov. 12, 2024, total 2 pages.
KIPO, Notice of Allowance of KR 10-2021-0105598 dated Dec. 14, 2023.
Wonseok Choi, PhD et al., "Three-dimensional Multistructural Quantitative Photoacoustic and US Imaging of Human Feet in Vivo", Radiolog, vol. 303, No. 2 (Feb. 22, 2022.).
Chenghung Yeh et al., "Microvascular quantification based on contour-scanning photoacoustic microscopy", Journal of Biomedical Optics 19(9), 096011 (Sep. 2014).
Changyeop Lee et al., "Three-dimensional clinical handheld photoacoustic/ultrasound scanner", Photoacoustics 18 (2020) 100173, Mar. 11, 2020.

* cited by examiner

[Fig. 1]
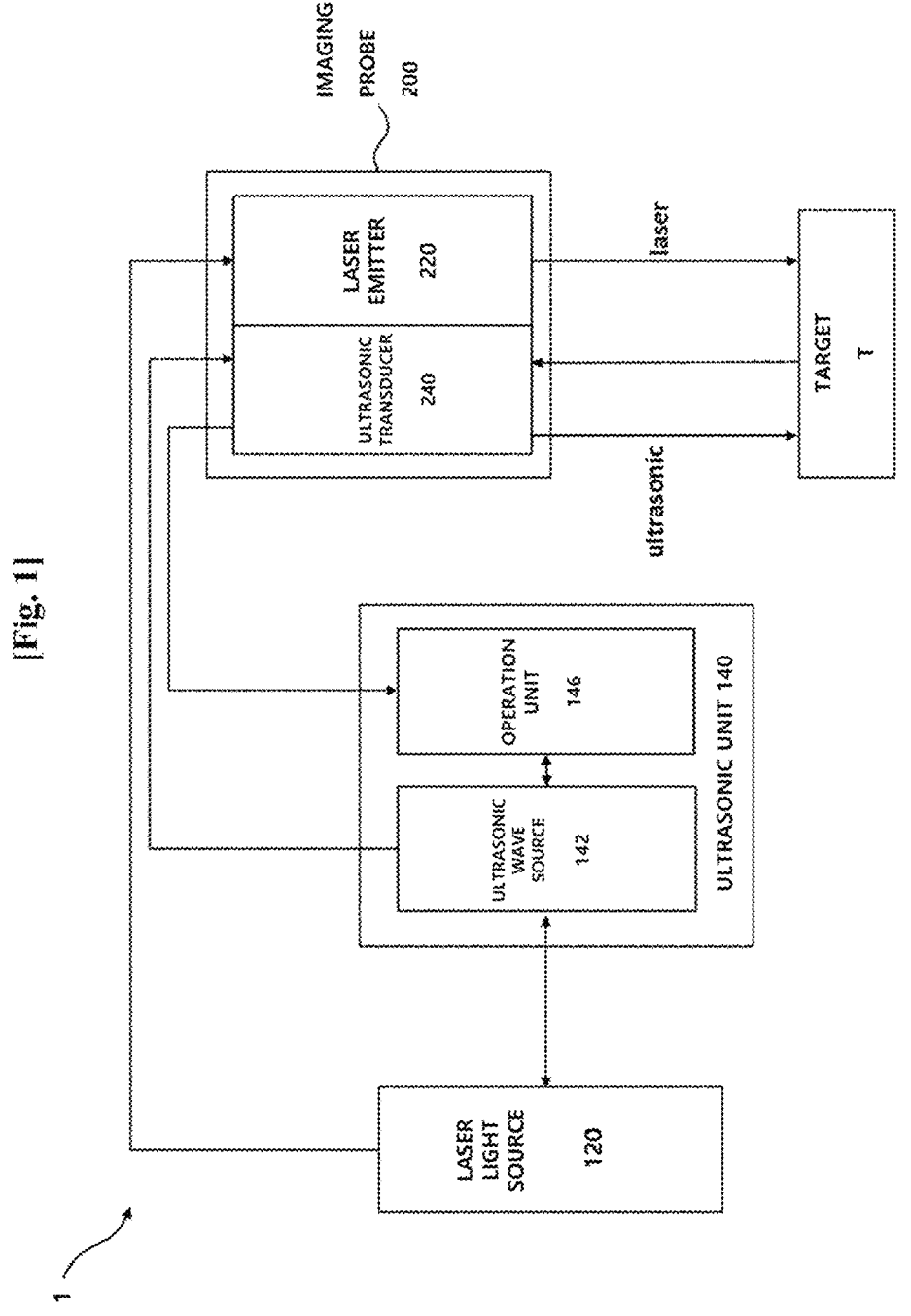

[Fig. 2]
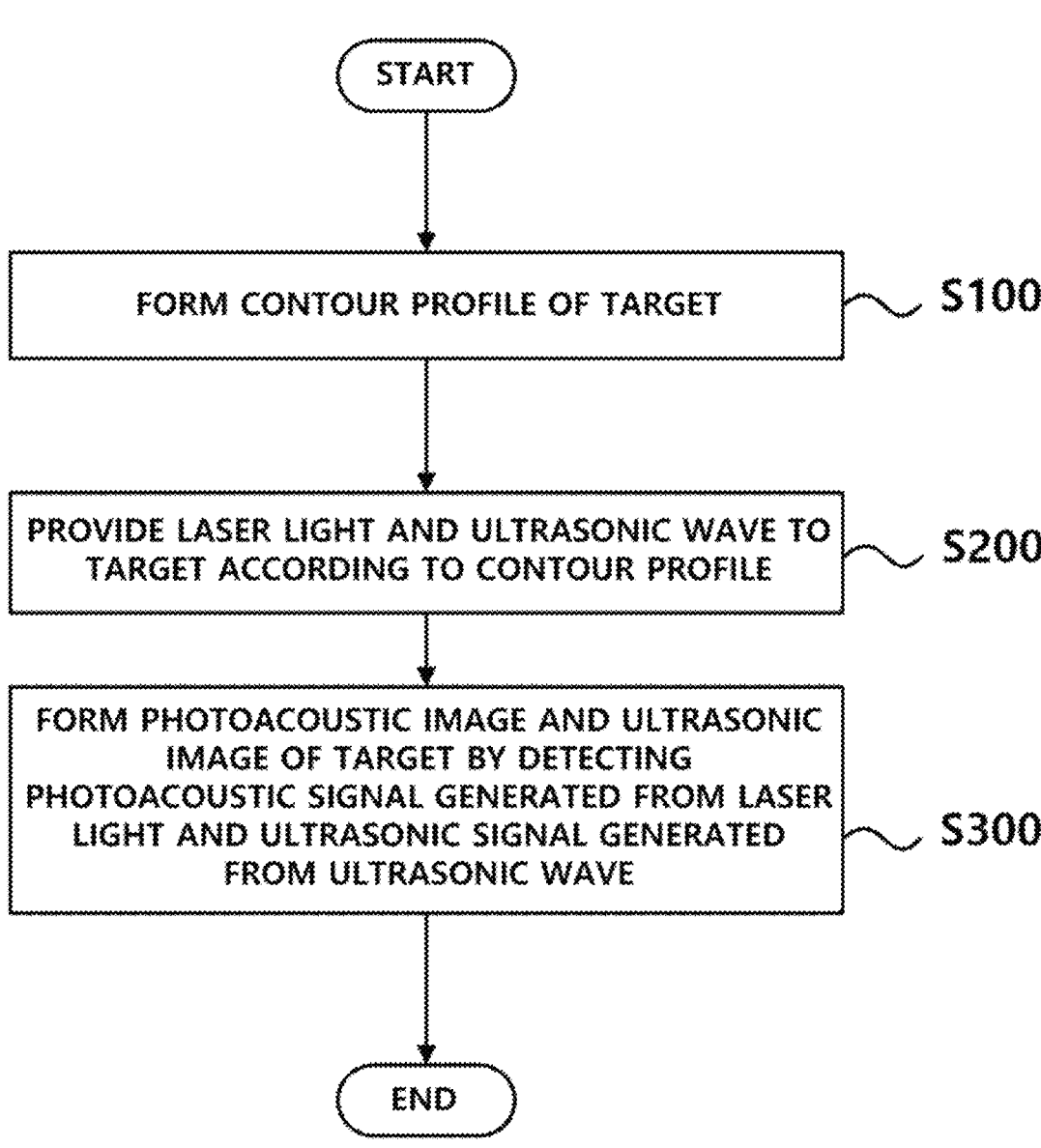

[Fig. 3]
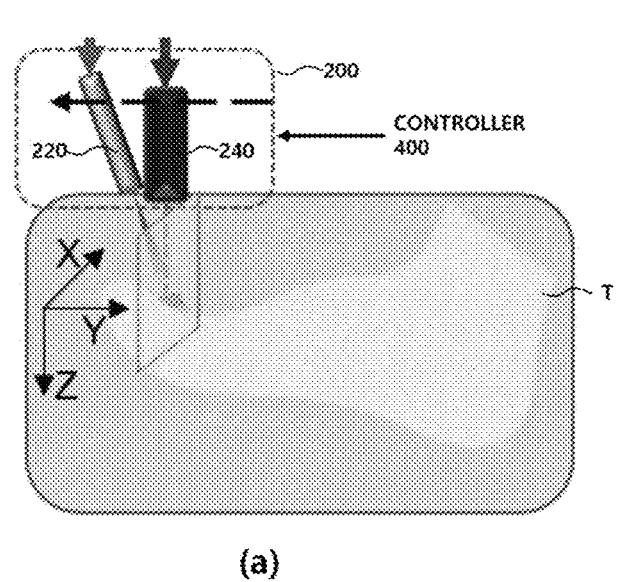
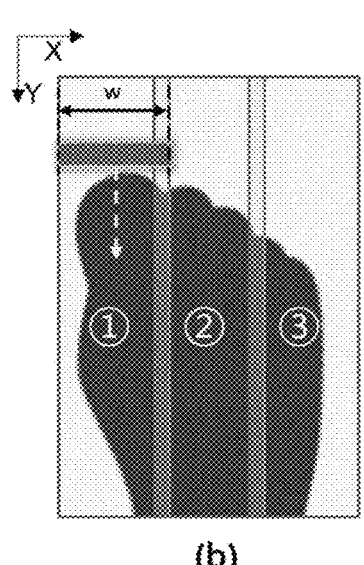
(a)                                        (b)
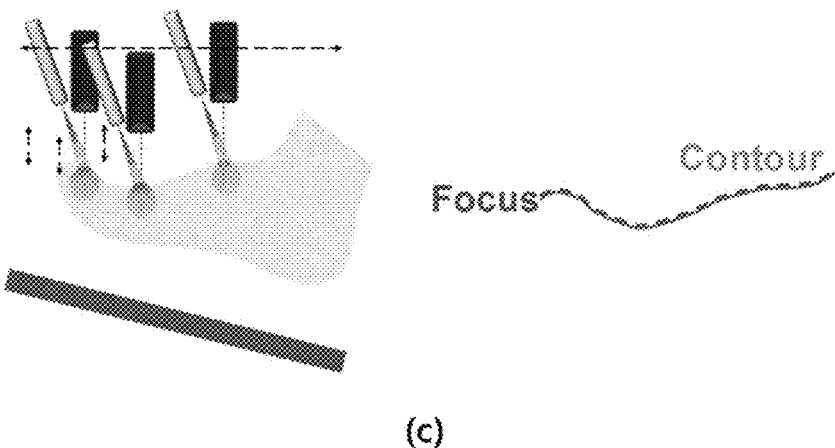
(c)

[Fig. 4]
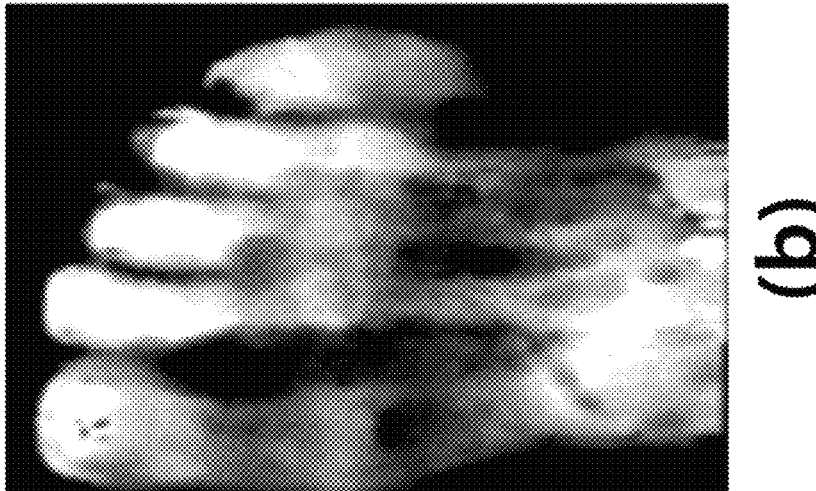
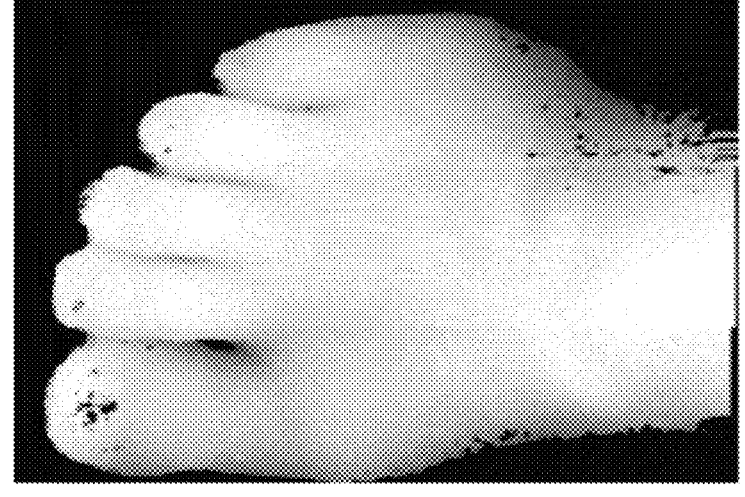

[Fig. 5]
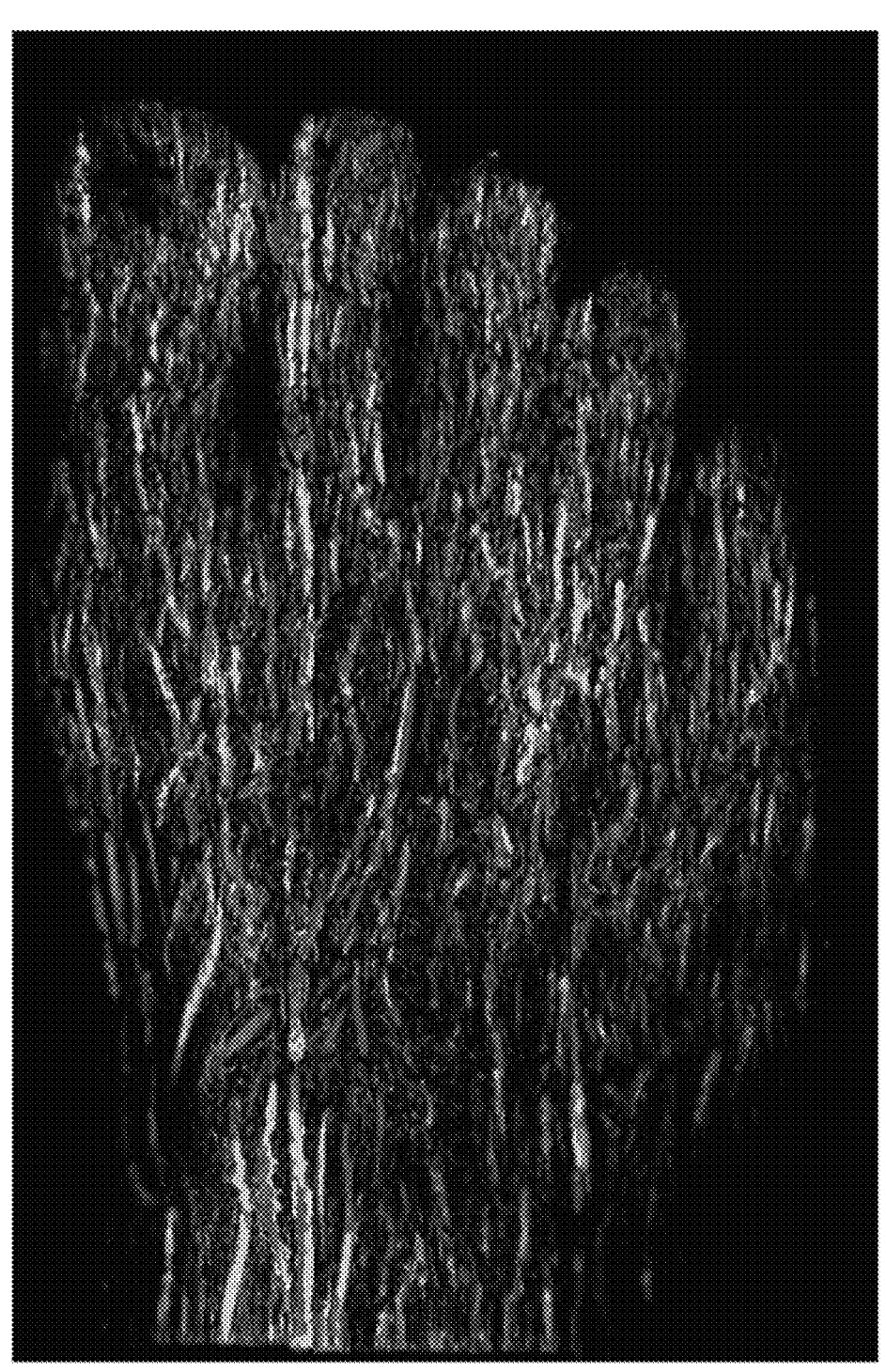

[Fig. 6]
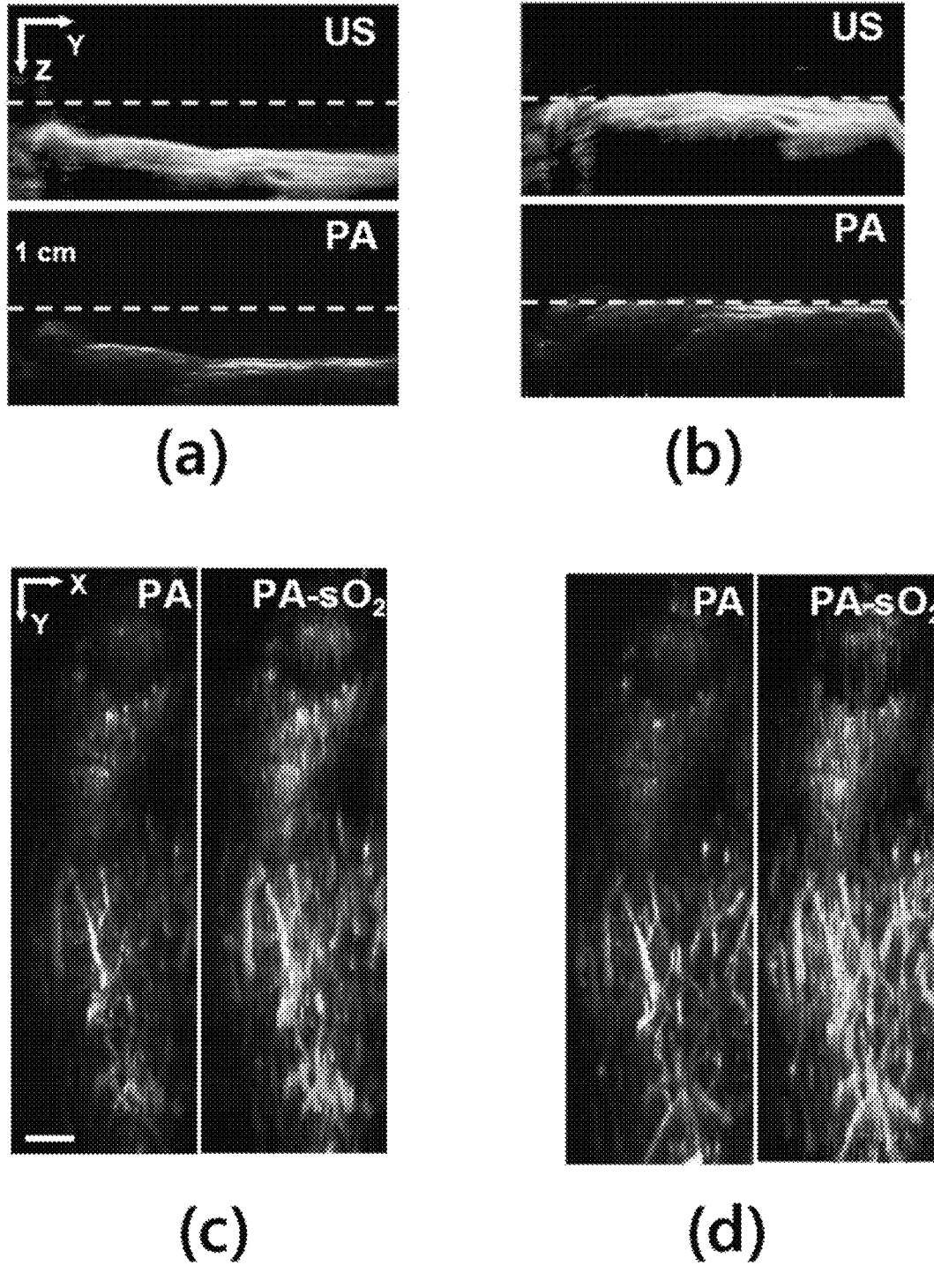
(a)                    (b)
(c)                    (d)

[Fig. 7]
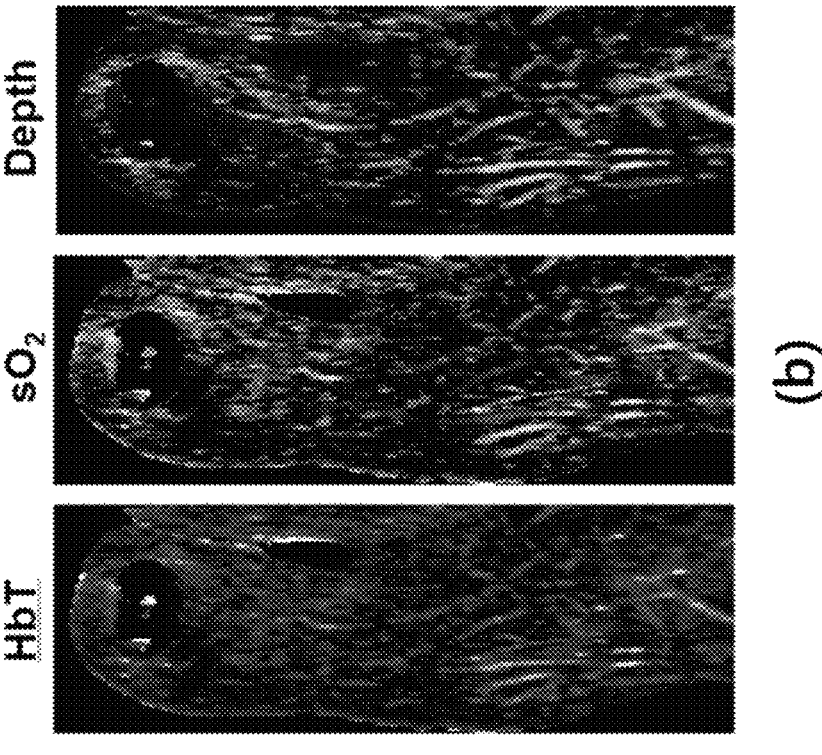
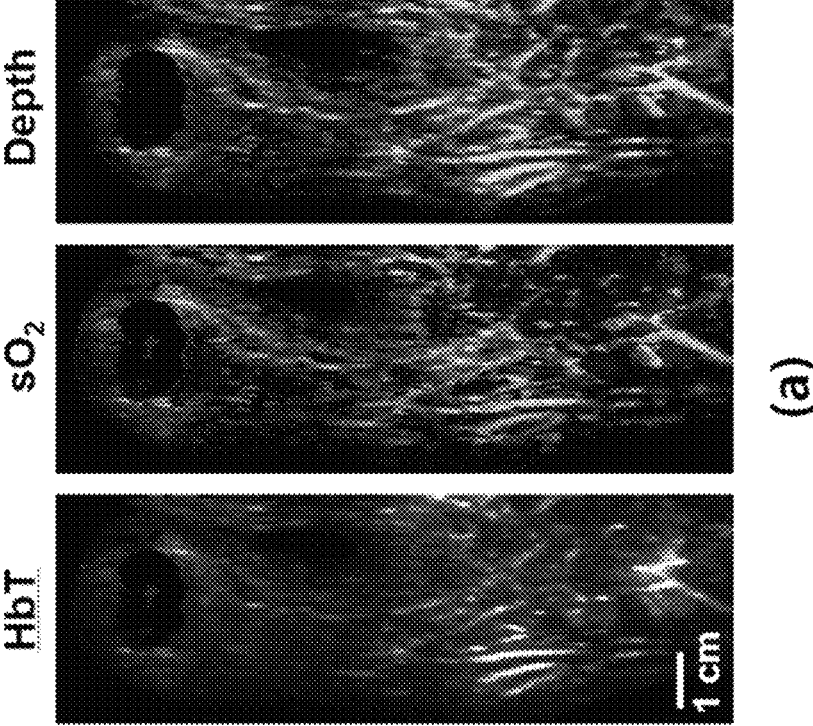

[Fig. 8]
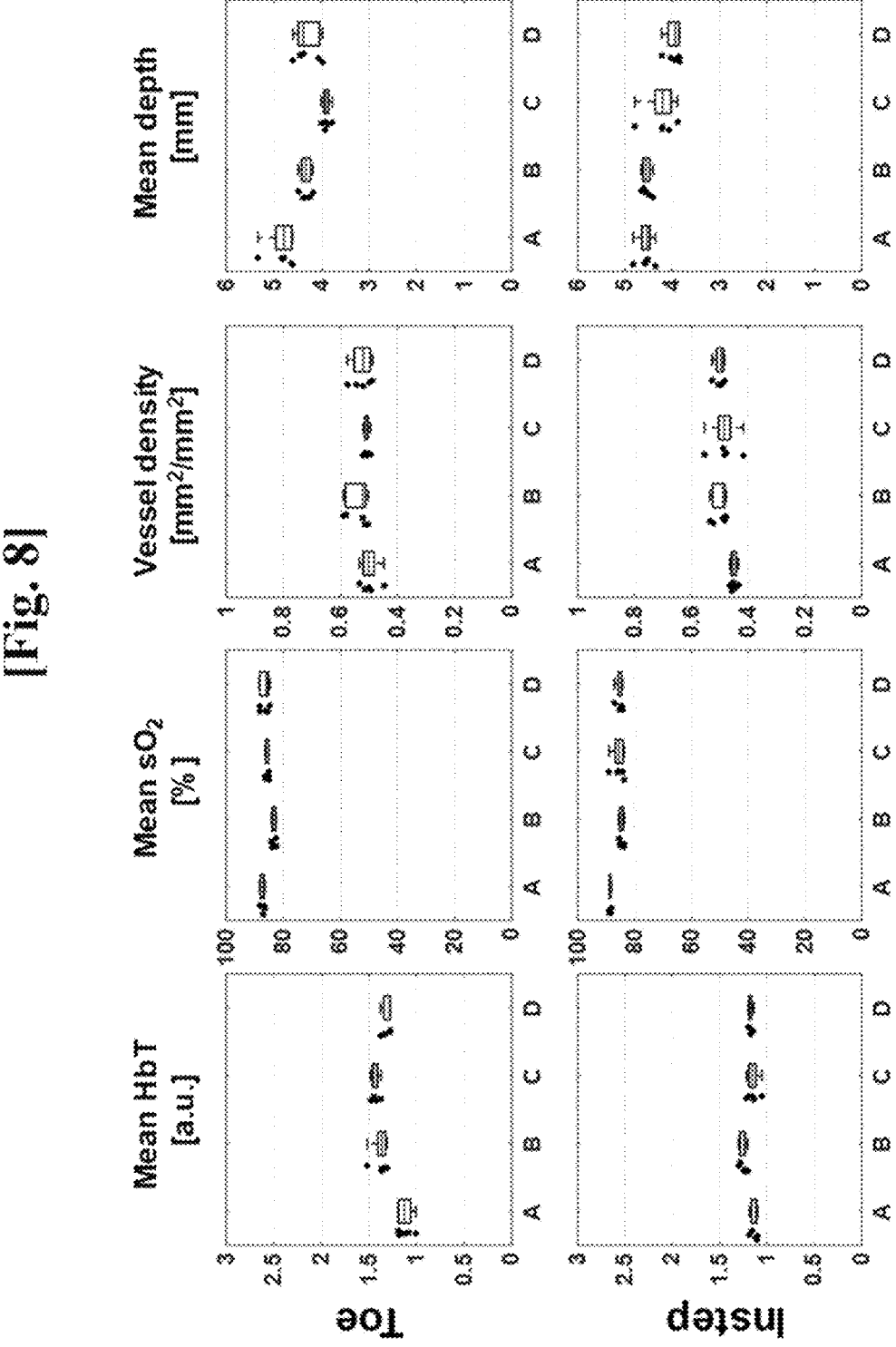

PHOTOACOUSTIC AND ULTRASONIC IMAGING DEVICE, AND IMAGING FORMING METHOD

TECHNICAL FIELD

The present disclosure relates to a photoacoustic and ultrasonic imaging device and a method of forming a photoacoustic image and an ultrasound image.

BACKGROUND ART

A peripheral vascular image is important for evaluating blood circulation in a patient with a peripheral arterial disease. Many vascular imaging technologies, such as a Doppler ultrasonic image, computed tomography (CT) or magnetic resonance (MR) angiography, are performed for clinical use but a spatial resolution for visualizing microvessels is generally low. CT and MR angiography are not suitable for a regular checkup because a contrast medium should be injected to obtain an image of blood vessels. Doppler ultrasonography is relatively safe but resolution is low.

DETAILED DISCLOSURE OF INVENTION

Technical Problem

Embodiments are directed to providing an image from a high-resolution dual-mode photoacoustic (PA) image/ultrasonic image on the basis of structural information of an ultrasonic image.

Technical Solution

A photoacoustic and ultrasonic imaging device according to an embodiment includes a laser light source configured to generate a laser, an ultrasonic wave source configured to generate an ultrasonic wave generation signal, an imaging probe including a laser emitter configured to receive the laser and emit the laser to a target and an ultrasonic transducer configured to receive the ultrasonic wave generation signal, emit an ultrasonic wave to the target, and detect a photoacoustic signal and an ultrasonic signal generated and reflected from the target, and an operation unit configured to form an image of tissue in the target from the laser and an image of tissue in the target from the ultrasonic wave on the basis of the ultrasonic signal detected by the ultrasonic transducer.

According to an aspect of an embodiment, the imaging probe may emit the laser and the ultrasonic wave while moving along a contour profile of the target.

According to an aspect of an embodiment, the laser light source may form and provide laser having two or more different wavelengths.

According to an aspect of an embodiment, the image of the tissue in the target may be an image of blood vessels in the target.

According to an aspect of an embodiment, the image of the tissue in the target from the ultrasonic wave may include at least one of an image of blood vessels in the target, an image of the skin of the target, and an image of bones of the target.

According to an aspect of an embodiment, the ultrasonic transducer may include a plurality of transducers configured to provide the ultrasonic wave to the target and arranged in an array.

According to an aspect of an embodiment, the photoacoustic and ultrasonic wave imaging device may further include a distance sensor, and the distance sensor may form a contour profile of the target by detecting a distance to the target before the laser is emitted to the target.

According to an aspect of an embodiment, the ultrasonic wave source may control the laser light source and the ultrasonic transducer to emit the laser and the ultrasonic wave in synchronization with each other.

According to an aspect of an embodiment, the photoacoustic and ultrasonic imaging device may further include an examination table configured to place the target thereon, and the examination table may include a target fixing part configured to fix the target, a moving structure configured to place and move the imaging probe on the target, and a container filled with a medium for delivering an ultrasonic wave and a photoacoustic signal between the target and the imaging probe.

A method of forming a photoacoustic image and an ultrasonic image of a target according to an embodiment includes (a) forming a contour profile of the target, (b) providing laser light and an ultrasonic wave to the target according to the contour profile, and (c) forming a photoacoustic image and an ultrasonic image of the target by detecting a photoacoustic signal generated from the laser light and an ultrasonic signal generated from the ultrasonic wave.

According to an aspect of an embodiment, operation (a) may include forming the contour profile of the target by calculating a distance to the target using an ultrasonic transducer or a distance sensor.

According to an aspect of an embodiment, operation (b) may include maintaining a constant distance between the target and an ultrasonic transducer and a constant distance between the target and a laser emitter.

According to an aspect of an embodiment, operation (b) may be performed after the forming of the contour profile of the entire target.

According to an aspect of an embodiment, operation (a) may be performed on a certain area of the target, and operation (b) may be performed while moving along a contour profile of the area.

According to an aspect of an embodiment, the forming of the photoacoustic image of the target may include detecting a background signal for surrounding tissues, calculating a representative value of the background signal, and compensating an image of the target on the basis of the representative value of the background signal.

According to an aspect of an embodiment, the representative value may be the average brightness of the background signal.

According to an aspect of an embodiment, the compensating of the image of the target may include dividing the pixel intensity of the photoacoustic image by the representative value According to an aspect of an embodiment, the ultrasonic wave and the laser may be emitted in synchronization with each other.

According to an aspect of an embodiment, operation (b) may be performed by two or more laser beams having different wavelengths, and operation (c) may include forming a photoacoustic image from the emitted two or more laser beams having different wavelengths.

According to an aspect of an embodiment, the method may further include (d) calculating a hemoglobin concentration, a blood oxygen saturation, a vessel distribution density and a vessel depth from the photoacoustic image and the ultrasonic image.

According to an aspect of an embodiment, the method may further include (d) calculating a hemoglobin concentration, a blood oxygen saturation, a vessel distribution density and a vessel depth from the photoacoustic image and the ultrasonic image.

Advantageous Effects

Embodiments provide a multi-structure image extracted from a combination of images of various structures (e.g., skin, bones, and blood vessels) with a photoacoustic vascular image. In addition, the resolution of an image can be improved by performing scanning along a contour of a target using a contour scan technique.

DESCRIPTION OF DRAWINGS

FIG. 1 is a block diagram of an overview of a photoacoustic/ultrasonic imaging device (1) according to an embodiment.

FIG. 2 is a flowchart of an overview of a photoacoustic and ultrasonic imaging method according to an embodiment.

FIGS. 3(a), 3(b), and 3(c) are schematic diagrams illustrating an operation of a photoacoustic/ultrasonic imaging device according to an embodiment.

FIG. 4(a) is an example of an image of the skin obtained from an ultrasonic volumetric image.

FIG. 4(b) is an example of an image of bones obtained from an ultrasonic volumetric image.

FIG. 4(c) is an example of a vascular image obtained from an ultrasonic volumetric image.

FIG. 5 is an example of a photoacoustic image of microvessels of a foot that is a target (T).

FIG. 6(a) is a view of an ultrasonic image (US) and a photoacoustic image (PA) obtained by moving an imaging probe linearly according to the related art, and FIG. 6(b) is view of an ultrasonic image (US) and a photoacoustic image (PA) obtained by moving an imaging probe according to a contour profile of a target according to an embodiment. A left diagram of FIG. 6(c) is a vascular image (PA) obtained in the form of a photoacoustic image by moving an imaging probe linearly according to the related art, and a right diagram of FIG. 6(c) is a photoacoustic image showing oxygen saturation (PA-sO$_2$). A left diagram of FIG. 6(d) is a vascular image (PA) obtained in the form of a photoacoustic image by moving an imaging probe according to a contour profile of a target according to an embodiment, and a right diagram of FIG. 6(d) is a photoacoustic image showing oxygen saturation (PA-sO$_2$).

FIG. 7(a) illustrates a hemoglobin concentration (HbT), oxygen saturation (sO$_2$), and a subcutaneous blood vessel depth (Depth) obtained by a photoacoustic image (PA) technique of the related art, and FIG. 7(b) illustrates a hemoglobin concentration (HbT), oxygen saturation (sO$_2$), and a subcutaneous blood vessel depth (Depth) obtained by a photoacoustic image (PA) technique for compensating an image of tissue in a target (T) according to an embodiment.

FIG. 8 is a graph showing averages of total hemoglobin concentrations (HbT), oxygen saturations (sO$_2$), vessel densities and mean depths of four different people that were measured five times according to an embodiment.

MODES OF THE INVENTION

Hereinafter, embodiments will be described with reference to the accompanying drawings.

FIG. 1 is a block diagram of an overview of a photoacoustic/ultrasonic imaging device 1 according to an embodiment. Referring to FIG. 1, the photoacoustic/ultrasonic imaging device 1 includes a laser light source 120 for forming a laser, an ultrasonic wave source 142 for forming an ultrasonic wave generation signal, an imaging probe 200 that includes a laser emitter 220 for receiving the laser and emitting the laser to a target T and an ultrasonic transducer 240 for receiving the ultrasonic wave generation signal, emitting an ultrasonic wave to the target, and detecting a photoacoustic image and an ultrasonic signal generated from the target, and an operation unit 146 configured to form an image of tissue in the target T by the laser and an image of tissue in the target T by the ultrasonic wave on the basis of the ultrasonic signal detected by the ultrasonic transducer 240.

Referring to FIG. 1, the photoacoustic/ultrasonic imaging device 1 according to the embodiment includes a laser light source 120 and an ultrasonic unit 140. The laser light source 120 forms a laser having a predetermined wavelength. For example, the laser provided by the laser light source 120 may be a pulse laser with a pulse repetition rate of 1 Hz to 20 Hz. For example, the laser light source 20 may control light to be provided and may be, for example, a Phocus Mobile product manufactured by OPOTEK Inc. The laser light source 120 may form and provide a plurality of laser beams having different wavelengths.

The ultrasonic unit 140 may include the ultrasonic wave source 142 and the operation unit 146 configured to receive a signal detected by the ultrasonic transducer 240 and perform imaging. In the embodiment shown in FIG. 1, the operation unit 146 is included in the ultrasonic unit 140. However, in an embodiment not shown herein, an operation unit may be a separate component configured to receive a signal detected by an ultrasonic transducer and perform imaging after performing an operation on the signal to form an image.

The ultrasonic wave source 142 forms and provides an ultrasonic wave of a predetermined frequency. In an embodiment, the ultrasonic wave provided by the ultrasonic wave source 142 may be an ultrasonic wave having a center frequency of 5.5 MHz to 11.5 MHz. For example, the ultrasonic wave source 142 may be an ultrasonic system ECUBE 12R manufactured by Alpinion Medical Systems Co. Ltd.

When a laser has a pulse repetition rate of 10 Hz, one photoacoustic image can be obtained from one or more consecutive laser pulses and an available frame rate may be 10 Hz or less for both a photoacoustic image and an ultrasonic image (US). However, this is only an example, and an available frame rate may be higher or lower than 10 Hz.

The imaging probe 200 includes the laser emitter 220 configured to receive a laser and provide the laser to a target T and one or more ultrasonic transducers 240 configured to receive an ultrasonic wave and provide the ultrasonic wave to the target T. In an embodiment, the laser emitter 220 may include a plurality of optical fiber bundles connected to the laser light source 120, and emit a linear laser to the target T. The ultrasonic transducer 240 may include one or more transducers arranged in an array, e.g., 128 transducers arranged in an array. This is only exemplary. The ultrasonic transducer 240 receives an ultrasonic wave generation signal provided from the ultrasonic wave source 142, forms an ultrasonic wave corresponding to the ultrasonic wave generation signal, and provides the ultrasonic wave to the target T. The ultrasonic transducer 240 and the laser emitter 220 may each be moved by a motor drive (not shown) controlled by a controller.

The ultrasonic transducer 240 and the laser emitter 220 included in the imaging probe 200 are provided such that a laser beam from the laser emitter 220 and an ultrasonic wave from the ultrasonic transducer 240 match an image plane at a predetermined location below the imaging probe 200. In an embodiment, the laser beam and the ultrasonic wave are provided to coincide with each other 10 to 50 mm below the imaging probe 200 and may coincide with each other, for example, at a depth of 30 mm in the target T.

The ultrasonic wave from the ultrasonic transducer 240 is provided to the target T. An ultrasonic signal corresponding to the tissue and structure in the target T is generated from the provided ultrasonic wave and provided to the outside of the target T.

The laser light provided to the target T from the laser emitter 220 is absorbed into the tissue in the target T. A signal in an ultrasonic band corresponding to the tissue in the target T absorbing the laser light is formed and provided to the outside of the target T.

Ultrasonic signals provided from the target T are detected by the ultrasonic transducer 240. An ultrasonic signal detected by the ultrasonic transducer 240 is provided to the operation unit 146. The operation unit 146 detects a signal generated from a laser provided to the target T and forms a photoacoustic image using, for example, a Fourier domain reconstruction technique.

The operation unit 146 detects a signal, which is formed in the target T, from an ultrasonic wave provided to the target T and reconstructs an ultrasonic image by performing, for example, delay-and-sum beamforming. In an embodiment, a reconstructed photoacoustic image and ultrasonic image may each be generated, displayed and stored in the form of an image signal by the operation unit 146.

In an embodiment not shown herein, an imaging probe may further include a distance sensor configured to obtain a contour profile of a target by measuring a distance to the target.

An operation of the photoacoustic/ultrasonic imaging device 1 having the above configuration will be described below. FIG. 2 is a flowchart of an overview of a photoacoustic and ultrasonic imaging method according to an embodiment. Referring to FIG. 2, a method of forming a photoacoustic image and an ultrasonic image according to the embodiment includes (a) forming a contour profile of a target (S100), (b) providing laser light and an ultrasonic wave to the target according to the contour profile (S200), and (c) forming the photoacoustic image and the ultrasonic image of the target by detecting a photoacoustic signal generated from the laser light and an ultrasonic signal generated from the ultrasonic wave (S300).

A contour of the target T is obtained by scanning the target T with the ultrasonic transducer 240. In an embodiment, an ultrasonic image of the skin is obtained using the ultrasonic transducer 240. A process of detecting the skin is preferably simplified to quickly perform a process of obtaining an image of the skin so as to obtain a contour. In an embodiment, the process of detecting the skin may be performed by setting a threshold according to the strength of an ultrasonic wave and performing a smoothing process using boxcar or median filtering. A contour profile corresponding to a height of the target T is obtained by selecting a median on the obtained ultrasonic image of the skin in an X-axis direction.

The obtained contour profile corresponding to the height of the target T is used for the imaging probe 200 to perform scanning at a constant speed in a Y-axis direction and control a motor drive (not shown) to be moved in a Z-axis direction according to the height of the target T.

The obtaining of the contour according to the embodiment may be performed before photoacoustic/ultrasonic imaging the target T. In an embodiment, the photoacoustic/ultrasonic imaging may be performed after the obtaining of the contour. That is, after the contour of the target T is obtained, the photoacoustic/ultrasonic imaging may be performed according to the obtained contour. In another embodiment, a contour of a predetermined portion of the target T may be obtained, photoacoustic/ultrasonic imaging may be performed on the predetermined portion according to the contour, and the obtaining of a contour and the performing of photoacoustic/ultrasonic imaging may be repeatedly performed. In an embodiment not shown herein, the obtaining of the contour may be performed by a distance sensor.

FIGS. 3(a), 3(b), and 3(c) are schematic diagrams illustrating an operation of a photoacoustic/ultrasonic imaging device according to an embodiment. In the embodiment of FIGS. 3(a), 3(b), and 3(c), a case in which a target T is a human foot is shown. However, the case is only an example and an object to be detected, e.g., the foot, the hand, the thigh, the calf, the upper arm, the forearm or the torso, may be set as the target T.

The target T may be placed on an examination table (not shown) to perform an imaging process on the target T. The examination table may include a target fixing part (not shown) for fixing the target T during the imaging process. The examination table may include a moving structure (not shown) including rails and a frame for allowing an imaging probe 200 to perform imaging while moving on the target T. The moving structure may be an electric moving structure for moving the imaging probe 200 in directions of X, Y, and Z axes.

The examination table may include a container (not shown) for immersing the target T into a medium, and the container is filled with a medium for delivering an ultrasonic wave and a photoacoustic signal. In an embodiment, the target fixing part may fix the target T by immersing the target T into the container, and a liquid into which the target T is immersed may be water.

In the embodiment of FIGS. 3(a) and 3(c), the imaging probe 200 moves along the Y-axis, and the operation unit 146 forms a volumetric image by stacking a photoacoustic/ultrasonic image obtained at each position to which the imaging probe 200 moves.

A step size by which the imaging probe 200 is moved by an electric stage (not shown) in the Y-axis direction may be less than a −6 dB beam width of an ultrasonic transducer array. For example, a step size by which the imaging probe 200 moves in the Y-axis direction may be less than 0.5 mm.

A width w by which the imaging probe 200 scans the target T by providing a laser and an ultrasonic wave to the target T may be less than a width of the target T. In this case, a photoacoustic image and an ultrasonic image of the entire target T may be obtained by performing scanning a plurality of times while the target T is fixed.

As shown in FIG. 3(c), a process of providing a laser and an ultrasonic wave and performing scanning with the imaging probe 200 may be performed by adjusting a height of the imaging probe 200 to correspond to a contour profile of a target. Therefore, imaging is performed by adjusting a focus of the imaging probe 200 to correspond to the contour profile as shown in a right part of FIG. 3(c). Accordingly, it is possible to obtain an image having a higher resolution than in the related art.

To obtain an image of the entire target T, scanning is performed and a photoacoustic image and an ultrasonic image obtained by scanning are merged by computer software to form a three-dimensional (3D) image. In an embodiment, an image of the entire target T may be obtained by performing scanning a plurality of times. In an embodiment, the 3D image may be obtained by computer software.

In an embodiment, in order to reconstruct structural information of an original contour of a photoacoustic/ultrasonic image obtained at the same height as the target T by scanning a contour, a height of this image may be adjusted according to a height of the contour and a plurality of scanning results may be merged by computer software.

A volumetric image may be obtained from the photoacoustic/ultrasonic image of the entire target T, and essential components of the target T are extracted. An ultrasonic volumetric image of a target shows a variety of structures, such as the skin (hyperechoic), bones (which is hyperechoic but a lower part thereof is non-echoic), and blood vessels (which are hyperechoic but the inside of which is non-echoic), according to brightness.

FIG. 4(a) is an example of an image of skin obtained from an ultrasonic volumetric image. An ultrasonic image of the skin is obtained by detecting a position of the skin by detecting a smooth surface from brightness information. For example, the detecting of a smooth surface may be performed with computer software as described above.

FIG. 4(b) is an example of an image of bone obtained from an ultrasonic volumetric image. In the ultrasonic image, the bones are darker than the skin but appear as bright dots. After information about the skin is obtained, a pixel intensity adjustment process is performed to reduce the brightness of the skin and to increase the brightness of the bones and thereafter the bones may be detected by software. For example, an image of the bones may be obtained by detecting a boundary of the bones by a Log-Gabor filter or by inverting pixel intensity and detecting a contour of lower parts of the bones with computer software.

FIG. 4(c) is an example of a vascular image obtained from an ultrasonic volumetric image. In the ultrasonic image, the inside of blood vessels is displayed dark (low brightness). Due to color inversion, the inside of the block vessels looks bright, and a vascular image may be obtained by determining whether pixels corresponding to blood in the blood vessels are connected in the form of a blood vessel using a Frangi filter.

FIG. 5 is an example of a photoacoustic image of microvessels of a foot that is a target T. Laser light provided from the laser emitter 220 is provided to the target T and penetrates the target T. Tissues in the target T absorb the penetrating laser light and provide a signal in an ultrasonic band to the outside. The operation unit 146 detects the signal in the ultrasonic band formed as described above to form a photoacoustic image.

However, because the laser light provided to the target T may scatter and the intensity of the laser light decreases as a depth to which the laser light penetrates the skin increases, signal processing is performed on a background signal to form an image with sufficient signal intensity. A background signal of tissue around blood vessels is formed from the laser light provided to the target T, and it is expected that a laser forming the background signal will attenuate with the same tendency as a laser provided to the tissue around the blood vessels.

Therefore, a representative value may be calculated by extracting the background signal excluding a vascular signal, and a tendency in which light attenuates may be identified by identifying a tendency of a representative value of a position in the target T. For example, the representative value of the background signal may be an average value of an intensity of the background signal within a certain area.

Therefore, the tendency of the representative value corresponds to a tendency of attenuation of the laser light penetrating the target T, and an image formed by compensating an image of tissue in the target T is substantially the same as an image of blood vessels in the target T shown in FIG. 5. For example, a method of compensating the image of tissue in the target T may be performed by dividing pixel intensity in a photoacoustic image of tissue by the tendency of the representative value.

Experimental Example

Experimental examples of an embodiment will be described with reference to the accompanying drawings below. FIG. 6(a) is a view of an ultrasonic image US and a photoacoustic image PA obtained by moving an imaging probe linearly according to the related art, and FIG. 6(b) is view of an ultrasonic image US and a photoacoustic image PA obtained by moving an imaging probe according to a contour profile of a target according to an embodiment. Referring to FIGS. 6(a) and 6(b), according to the related art, imaging was performed on a target below a focal plane indicated by a yellow broken line. However, according to an embodiment, imaging was performed on a target by moving an imaging probe according to a contour profile of the target and thus the target was imaged according to a focal plane.

Therefore, it can be seen that a resolution and signal strength of an image of FIG. 6(b) are greater than those of an image of FIG. 6(a) according to the related art.

A left diagram of FIG. 6(c) is a vascular image PA obtained in the form of a photoacoustic image by moving an imaging probe linearly according to the related art, and a right diagram of FIG. 6(c) is a photoacoustic image showing oxygen saturation PA-$sO_2$. A left diagram of FIG. 6(d) is a vascular image PA obtained in the form of a photoacoustic image by moving an imaging probe according to a contour profile of a target according to an embodiment, and a right diagram of FIG. 6(d) is a photoacoustic image showing oxygen saturation PA-$sO_2$.

Referring to FIGS. 6(c) and 6(d), it can be seen that a photoacoustic image of blood vessels and an image of an oxygen absorption rate obtained according to the embodiment are shown in greater detail, and thus the images have a higher resolution and a value close to an actual oxygen saturation, compared to the related art.

FIG. 7(a) illustrates a total hemoglobin concentration HbT, oxygen saturation $sO_2$, and a subcutaneous blood vessel depth Depth obtained by a technique of photoacoustic image PA of the related art, and FIG. 7(b) illustrates a hemoglobin concentration HbT, oxygen saturation $sO_2$, and a subcutaneous blood vessel depth Depth obtained by a photoacoustic image PA technique for compensating an image of tissue in a target T according to an embodiment.

For example, the total hemoglobin concentration HbT and the oxygen saturation $sO_2$ were measured based on the fact that an optical absorption rate of oxidized or non-oxidized hemoglobin varies according to a laser wavelength. Oxidized/non-oxidized hemoglobin concentrations at pixels of a photoacoustic image formed and obtained by emitting laser light having two or more wavelengths (four wavelengths in an embodiment) may be calculated using a linear equation, the total hemoglobin concentration HbT may be calculated by adding the oxidized/non-oxidized hemoglobin concentrations, and the oxygen saturation $sO_2$ may be calculated by dividing the oxidized hemoglobin concentration by the total hemoglobin concentration HbT.

For example, the subcutaneous blood vessel depth Depth may be calculated by detecting a position of the skin from an ultrasonic or photoacoustic image, a position of a pixel corresponding to each blood vessel may be calculated and expressed as a vertical distance from a position of a pixel of the skin, and when the position of the skin is detected from a photoacoustic image, the position of the skin may be detected from a melanin distribution form by calculating an optical absorption rate of the melanin component in the skin in a photoacoustic image, which is obtained from laser light having two or more wavelengths, using a linear equation, similar to the above description with respect to hemoglobin.

Referring to FIGS. 7(a) and 7(b), it can be seen from a diagram showing a total hemoglobin concentration HbT and a diagram showing oxygen saturation $sO_2$ and subcutaneous tissue Depth that an image formed by compensating an image of tissue in a target T according to an embodiment has a higher resolution.

FIG. 8 is a graph showing averages of total hemoglobin concentrations HbT, oxygen saturations $sO_2$, vessel densities and mean depths of four different people that were measured five times according to an embodiment. For example, a hemoglobin concentration HbT, oxygen saturation $sO_2$, and a mean depth may be calculated by selecting pixels each having a value greater than or equal to a threshold predetermined on the basis of an image of a total hemoglobin concentration HbT and calculating averages of hemoglobin concentrations HbT, oxygen saturations $sO_2$, and depths at positions of the selected pixels. For example, a vessel density may be calculated by dividing a total area occupied by pixels each having a value greater than or equal to the threshold predetermined on the basis of an image of a hemoglobin concentration HbT by a total area of the target T.

As shown in FIG. 8, a deviation between results measured from the four different people is not large. Thus, it can be seen from the results that in the embodiment, a possibility of reproduction is high.

Although the present disclosure has been described above with reference to embodiments shown in the drawings to help understand the present disclosure, the embodiments are only exemplary and it will be understood by those of ordinary skill in the art that various modifications may be made and equivalent embodiments may be implemented. Therefore, the scope of the present disclosure should be defined by the appended claims.

The invention claimed is:

1. A photoacoustic and ultrasonic imaging device comprising:
   a laser light source configured to generate a laser beam;
   an ultrasonic wave source configured to generate an ultrasonic wave generation signal;
   an imaging probe comprising: a laser emitter configured to receive the laser beam and emit the laser beam to a target; and an ultrasonic transducer configured to receive the ultrasonic wave generation signal, emit an ultrasonic wave to the target, and detect a photoacoustic signal and an ultrasonic signal generated and reflected from the target; and
   an operation unit configured to form an image of tissue in the target from the laser beam and an image of tissue in the target from the ultrasonic wave on the basis of the ultrasonic signal detected by the ultrasonic transducer, wherein the operation unit obtains a contour profile of the target from the ultrasonic wave emitted to the target from the ultrasonic transducer,
   wherein the imaging probe is configured to scan the target a plurality of times while the target is fixed when scanning width of the imaging probe is less than a width of the target, and
   photoacoustic images and ultrasonic images obtained by the scanning the target plurality of times are merged by a computer software,
   an examination table configured to place the target thereon,
   wherein the examination table comprises:
   a target fixing part configured to fix the target;
   a moving structure configured to place and move the imaging probe above the target; and
   a container configured to be filled with a medium for delivering the ultrasonic wave and the photoacoustic signal.

2. The photoacoustic and ultrasonic imaging device of claim 1, wherein the photoacoustic and ultrasonic wave imaging device further comprises a distance sensor,
   wherein the distance sensor detects a distance to the target, and
   the operation unit obtains the contour profile of the target from the distance detected by the distance sensor.

3. The photoacoustic and ultrasonic imaging device of claim 1, wherein the imaging probe is configured to emit the laser beam and the ultrasonic wave while moving along the contour profile of the target, and
   the operation unit is configured to form the image of the tissue in the target and adjust a size of the image according to the contour profile.

4. The photoacoustic and ultrasonic imaging device of claim 1, wherein the laser light source forms and provides a laser beam of two or more different wavelengths.

5. The photoacoustic and ultrasonic imaging device of claim 1, wherein the image of the tissue in the target from the laser beam comprises an image of one or more of the skin, background tissue, and blood vessels of the target.

6. The photoacoustic and ultrasonic imaging device of claim 1, wherein the image of the tissue in the target from the ultrasonic wave comprises one or more of an image of blood vessels in the target, an image of the skin of the target, and an image of bones of the target.

7. The photoacoustic and ultrasonic imaging device of claim 1, wherein the ultrasonic transducer comprises a plurality of transducers configured to provide the ultrasonic wave to the target and arranged in an array.

8. The photoacoustic and ultrasonic imaging device of claim 1, wherein the ultrasonic wave source controls the laser light source and the ultrasonic transducer to emit the laser beam and the ultrasonic wave in synchronization with each other.

9. A method of forming a photoacoustic image and an ultrasonic image of a target, the method comprising:
   (a) forming a contour profile of the target;
   (b) providing laser beam and an ultrasonic wave to the target according to the contour profile; and
   (c) forming a photoacoustic image and an ultrasonic image of the target by detecting a photoacoustic signal generated from the laser beam and an ultrasonic signal generated from the ultrasonic wave,
   wherein operation (a) comprises forming the contour profile of the target by calculating a distance to the target using an ultrasonic transducer, wherein the providing laser beam and an ultrasonic wave is performed plurality of times while the target is fixed when scanning width of an imaging probe is less than a width of the target, and wherein photoacoustic images and ultrasonic images obtained by the scanning of the plurality of times are merged by computer software, wherein the step (a), step (b) and step (c) are performed a photoacoustic and ultrasonic imaging device the photoacoustic and ultrasonic imaging device, comprises:

an examination table configured to place the target thereon, wherein the examination table comprises:

a target fixing part configured to fix the target;

a moving structure configured to place and move the imaging probe above the target; and a container configured to be filled with a medium for delivering the ultrasonic wave and the photoacoustic signal.

10. The method of claim 9, wherein operation (b) comprises maintaining a constant distance between the target and the ultrasonic transducer and a constant distance between the target and a laser emitter.

11. The method of claim 9, wherein operation (b) is performed after the forming of the contour profile of the entire target.

12. The method of claim 9, wherein operation (a) is performed on a certain area of the target, and operation (b) is performed while moving along a contour profile of the area.

13. The method of claim 9, wherein the forming of the photoacoustic image of the target comprises:

detecting a background signal for surrounding tissues;

calculating a representative value of the background signal; and compensating an image of the target on the basis of the representative value of the background signal.

14. The method of claim 13, wherein the representative value is average brightness of the background signal.

15. The method of claim 13, wherein the compensating of the image of the target comprises dividing a pixel intensity of the photoacoustic image by the representative value.

16. The method of claim 9, wherein operation (c) comprises forming an image of tissue in the target and adjusting a size of the image according to the contour profile.

17. The method of claim 9, wherein operation (b) comprises emitting the ultrasonic wave and the laser beam in synchronization with each other.

18. The method of claim 9, wherein operation (b) comprises emitting two or more laser beams having different wavelengths, and operation (c) comprises forming a photoacoustic image from the emitted two or more laser beams having different wavelengths.

19. The method of claim 9, further comprising (d) calculating a hemoglobin concentration, a blood oxygen saturation, a vessel distribution density and a vessel depth from the photoacoustic image and the ultrasonic image.

* * * * *